United States Patent [19]

Chapoteau et al.

[11] Patent Number: 5,096,831

[45] Date of Patent: * Mar. 17, 1992

[54] REAGENTS FOR DETERMINING CATIONS

[75] Inventors: Eddy Chapoteau, Brooklyn; Bronislaw P. Czech, Peekskill; Carl R. Gebauer, Crompond; Koon-Wah Leong, Ossining; Anand Kumar, Southfields, all of N.Y.

[73] Assignee: Miles Inc., Tarrytown, N.Y.

[*] Notice: The portion of the term of this patent subsequent to Sep. 3, 2008 has been disclaimed.

[21] Appl. No.: 699,188

[22] Filed: May 13, 1991

Related U.S. Application Data

[63] Continuation of Ser. No. 201,576, Jun. 1, 1988, Pat. No. 5,045,475, which is a continuation-in-part of Ser. No. 38,843, Apr. 15, 1987, Pat. No. 4,808,539.

[51] Int. Cl.$^5$ .................... G01N 21/78; G01N 33/20
[52] U.S. Cl. .......................... 436/74; 436/73; 436/79; 540/468; 540/469
[58] Field of Search .......... 436/73, 74, 79, 164, 436/169, 170; 540/468, 469

[56] References Cited

U.S. PATENT DOCUMENTS

| | | | |
|---|---|---|---|
| 3,872,212 | 3/1975 | Atwood et al. | 423/184 |
| 4,367,072 | 1/1983 | Vogtle et al. | 436/501 |
| 4,407,962 | 10/1983 | Tabacco et al. | 436/74 |
| 4,645,744 | 2/1987 | Charlton et al. | 436/74 |
| 4,670,218 | 6/1987 | Gantzer et al. | 422/56 |
| 4,703,015 | 10/1987 | Tabacco et al. | 436/74 |
| 4,808,539 | 2/1989 | Chapoteau et al. | 436/79 X |
| 4,843,158 | 6/1989 | Smith | 540/468 X |
| 4,845,212 | 7/1987 | Czech | 540/469 |
| 4,859,606 | 8/1989 | Cram et al. | 436/79 |
| 4,992,381 | 2/1991 | Cran et al. | 436/79 X |
| 4,994,395 | 2/1991 | Chapoteau et al. | 436/79 |

FOREIGN PATENT DOCUMENTS 0085320 8/1983 European Pat. Off.
0125555 11/1984 European Pat. Off.

Primary Examiner—Robert J. Hill, Jr.
Attorney, Agent, or Firm—Morgan & Finnegan

[57] ABSTRACT

The invention is reagents and procedures for determining an amount of cations present in a sample, the reagent including one or more chromogenic cryptand compounds of formula I

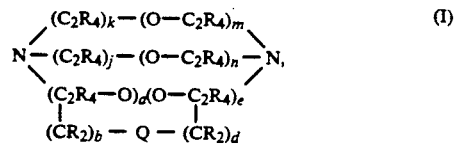

wherein
k and j, either same or different, are equal to 1 to about 5;
m and n, either same or different, are equal to 0 to about 4;
a and e, either same or different, are equal to 0 to about 2;
b and d, either same or different, are equal to 0 to about 5;
R, either same or different, is hydrogen, lower alkyl, lower alkylidene, lower alkenyl, allyl, or aryl; and

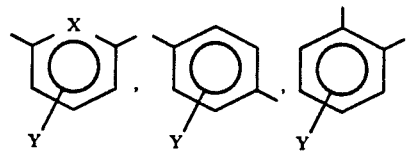

wherein
X is CH, N or COH; and
Y includes (Abstract continued on next page.)

5,096,831
Page 2

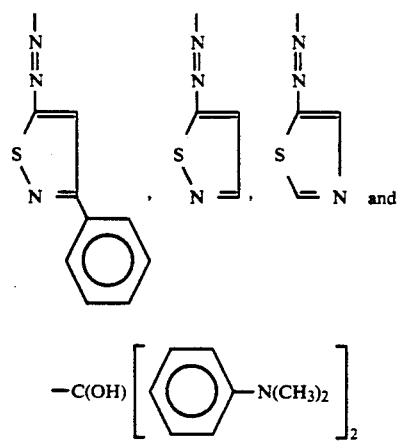

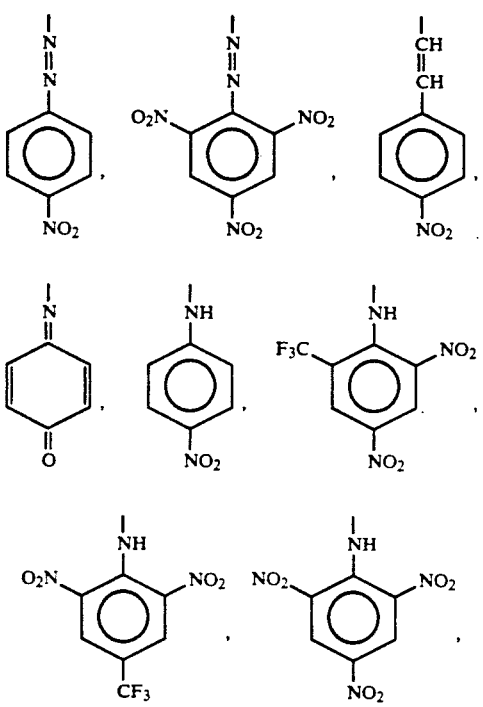

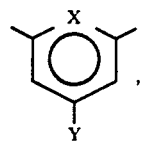

except that when Q is $$-C(OH)\left[\underset{}{\bigcirc}-N(CH_3)_2\right]_2$$

except that when Q is

[structure with X and Y substituents on benzene ring]

wherein Y is p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino or bis-(p-dimethylaminophenyl)hydroxymethyl, then the following condition cannot be present: that simultaneously b is equal to 0 or 1, d is equal to 0 or 1, j is equal to 1, n is equal to 1 or 2, a is equal to 1, e is equal to 1, k is equal to 1 and m is equal to 2.

11 Claims, 3 Drawing Sheets

REAGENTS FOR DETERMINING CATIONS

This is a continuation of application Ser. No. 07/201,576, filed June 1, 1988, now U.S. Pat. No. 5,045,475, which is a division of application Ser. No. 07/038,843, filed Apr. 15, 1987, now U.S. Pat. No. 4,808,539.

FIELD OF THE INVENTION

The present invention concerns compounds and reagents for simple and rapid determination of amounts of cations, and procedures for their use.

BACKGROUND OF THE INVENTION

The qualitative and quantitative determination of cations is of major significance in areas such as chemical and biochemical engineering for process control, in agriculture chemistry for soil research and fertilizer metering and in medicine for diagnostic and therapeutic determination of the potassium-sodium ratio. Present methods for cation determination include flame photometry and atomic absorption spectroscopy, both of which require sophisticated apparatus. Ion-sensitive cation electrodes on an ion-exchange basis generally yield sufficiently differentiated results, but are cumbersome to use.

Vogtle, U.S. Pat. No. 4,367,072 describes a process for determining ions. It is essentially based on selective complexing between the ion to be determined and a complexing agent and measurement of the extinction change occurring during complexation. The complexing agent is bonded with a chromophore.

The selective complexing agent may be an oligoether, oligoester or oligoamide, containing, for example, corand, cryptand or cyclic peptide and/or polyethylene glycol groups or other hetero atom-containing groups. The covalently or heteropolarly bound chromophore is a dye or fluorescent dye or a chromogen whose absorption spectra change through interaction with ions or lipophilic molecules through charge shifts or disturbances of the mesomeric system. This principle is well known in nature and in the art. Hemin, chlorophyll and metal complex dyes and metal indicators (e.g., zylenol orange and methylthymol blue based on the colorless complexing agent ethylenediaminetetraacetic acid (EDTA)) exhibit, to a greater or lesser extent, this general configuration.

A general problem of the above-cited complexing agents is that they usually are capable of reacting only in organic media, whereas the ion being determined is, as a rule, present in an aqueous solution. Although the aqueous solutions of the ions could be transformed in many cases to organic media by concentration, inclusion in organic salts, or solvent extraction, this would not satisfy the requirements of a practical and, if necessary, automated rapid method.

Klink, et al., European Patent Publication 85,320, disclose a potassium reagent and a procedure for determining potassium ions. The reagent contains a compound of general formula

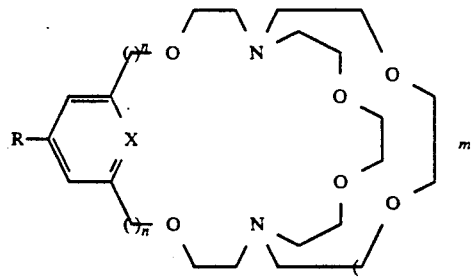

where n and m=0 or 1, X=N or COH and R=p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino and bis-(p-dimethylaminophenyl) hydroxymethyl. The potassium ions are determined in a reaction medium consisting of water and at least one water-miscible organic solvent and in the presence of an organic base.

Klink et al. do not recognize the interference from sodium ion in determination of potassium in EP 85,320. They provide extinction maxima data of various cations, and state that aside from the extinction maxima for rubidium, all other extinction maxima for the various cations tested are so far removed from potassium's extinction maxima that no interference occurs. However, Klink et al. base their conclusion on data obtained from isolated cation measurements, and fail to contemplate the effect on extinction maxima for these cations in mixed cation solutions.

The present invention is directed to novel compounds, reagents and methods which permit rapid determination of the presence of cations in a sample. The present invention also concerns reagents and methods permitting rapid determination of cations in single-phase aqueous media, wherein one of the improvements comprises use of one or more interfering cation complexing compound masks.

Certain cryptands have high selectivity for complexing with cations and, if coupled with chromophores, yield intensive color reactions that can be evaluated analytically. For example, it has been discovered that chromogenic cryptand 3.2.2 is particularly effective for potassium cation determination. Furthermore, it has been discovered that chromogenic cryptand 3.3.2 has good sodium cation selectivity. Determination of cations is further enhanced by using reagents of the present invention which may also contain one or more interfering cation complexing compound masks. For example, reagents and methods of the invention are effective for determining potassium ion concentration of a sample comprising a mixture of potassium and sodium ions. Reagents and methods of the invention are also effective for determining sodium ion concentration of a sample which comprises a mixture of large amount of sodium ions and potassium ions. These and other advantages will be more clearly described in the detailed description of the application.

SUMMARY OF THE INVENTION

The invention relates to compounds useful for determining amounts of cations present in a sample, the compounds being defined in formula I

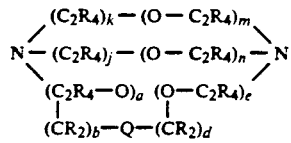
(I)

wherein k and j, either same or different, are equal to 1 to about 5;

m and n, either same or different, are equal to 0 to about 4;

a and e, either same or different, are equal to 0 to about 2;

b and d, either same or different, are equal to 0 to about 5;

R, either same or different, is hydrogen, lower alkyl, lower alkylidene, or lower alkenyl, allyl, or aryl; and —Q— is

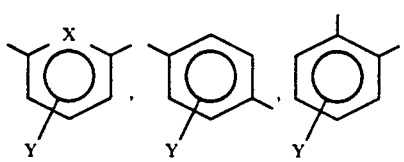

wherein
X is CH, N, or COH; and
Y includes

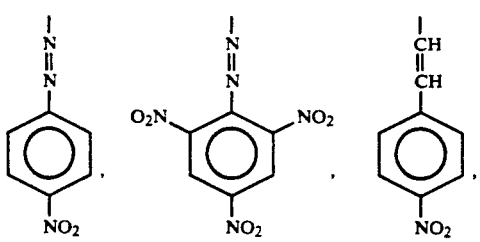

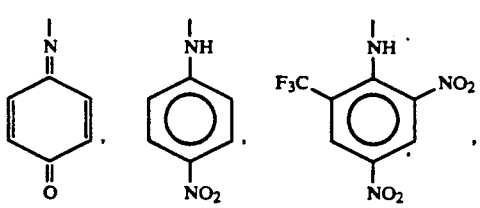

-continued

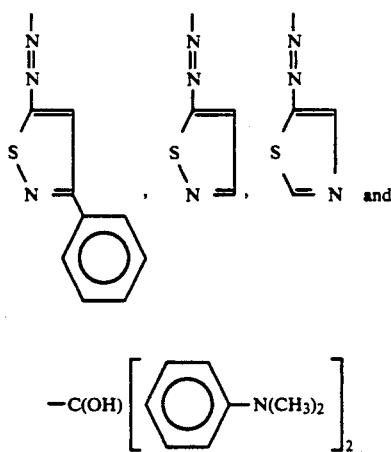

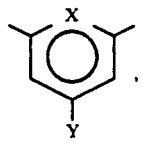

except that when Q is $$\begin{array}{c} X \\ \bigcirc \\ Y \end{array}$$

wherein Y is selected from the group consisting of p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino and bis-(p-dimethylaminophenyl) hydroxymethyl, then the following condition cannot be present: that simultaneously b is equal to 0 or 1, d is equal to 0 or 1, j is equal to 1, n is equal to 1 or 2, a is equal to 1, e is equal to 1, k is equal to 1 and m is equal to 2, and methods for detecting cations using these compounds.

The invention is also reagents comprising compound I which may contain one or more interfering cation complexing compound masks, and methods using said compounds and reagents for determining cations. Suitable interfering cation complexing compound masks are non-chromogenic and include spherands, hemispherands, cryptahemispherands, cryptands, and corands.

Spherands, hemispherands, and cryptahemispherands which are structurally oriented so as to complement a particular cation (i.e., to fit the size of that cation) are preferred in the present invention. Such masks may be referred to as "pre-organized".

Cryptands and corands which have cavity sizes matching particular cation diameters are also preferred in the present invention.

When the interfering cation is sodium, suitable masks include but are not limited to

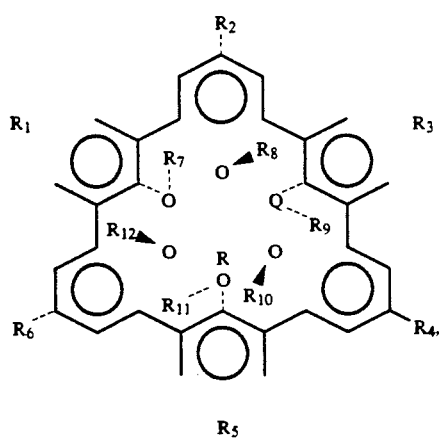

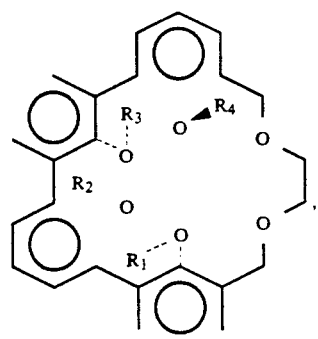

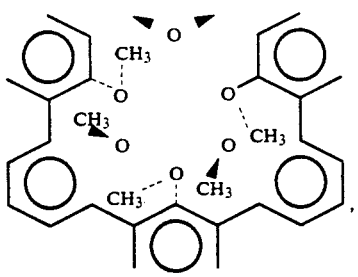

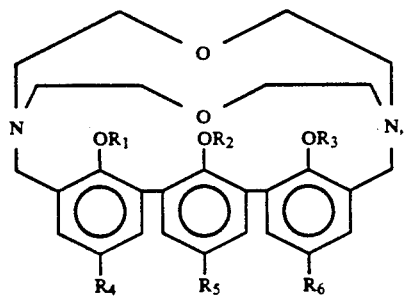

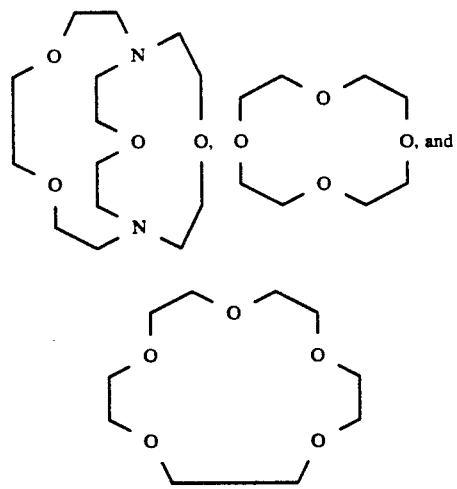

wherein $R_1$, $R_2$, $R_3$, $R_4$, $R_5$, $R_6$, $R_7$, $R_8$, $R_9$, $R_{10}$, $R_{11}$ and $R_{12}$, each either same or different, are hydrogen, lower alkyl, lower aryl, lower alkenyl, allyl or alkylidene. Kryptofix ® 2.1.1 cryptand is particularly effective as a sodium mask. Sodium ion masking is beneficial in determining potassium in a sample such as blood serum which contains a high concentration of sodium. The reagent further comprises one or more water-miscible organic solvents and a buffer. The reagent may comprise a surfactant.

When the interfering ion is potassium, suitable masks include but are not limited to

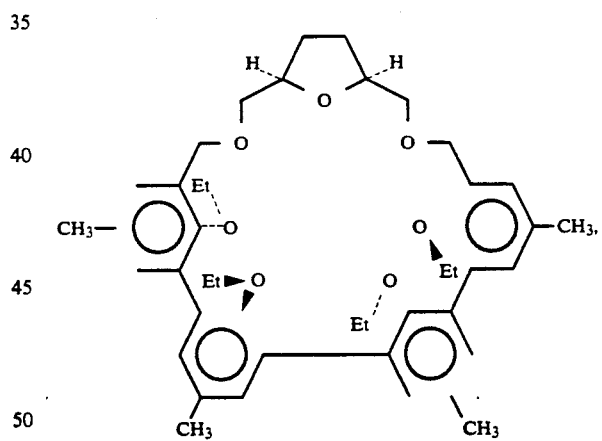

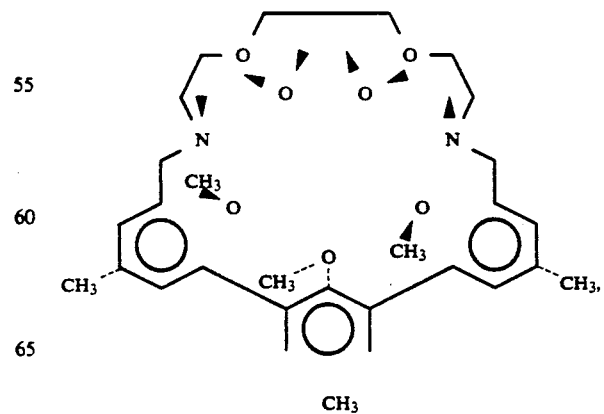

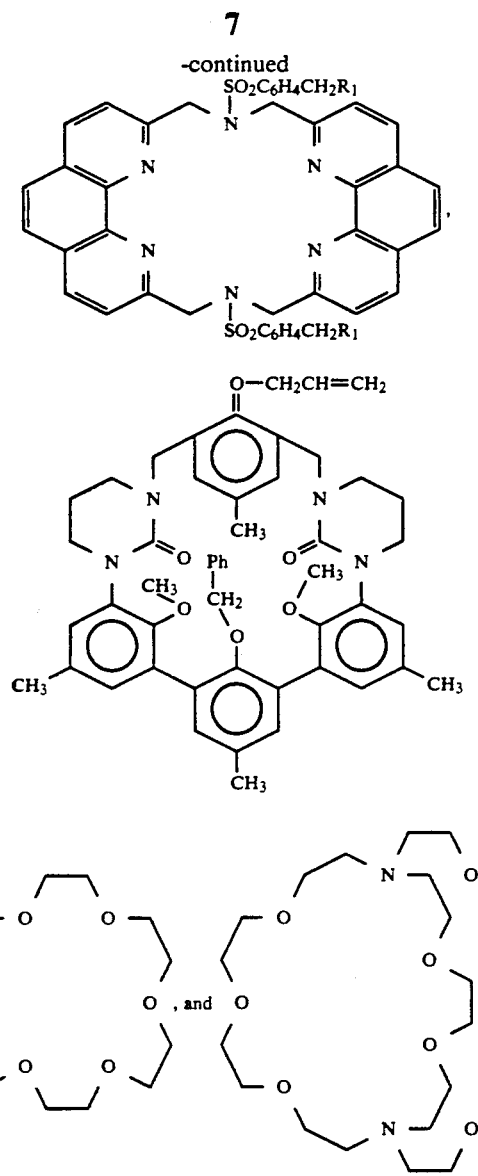

wherein $R_1$ is hydrogen lower alkyl, lower aryl, lower alkenyl, allyl or alkylidene. Cryptand 3.2.2 is particularly effective as a potassium mask.

DETAILED DESCRIPTION OF THE INVENTION

Figure 1:
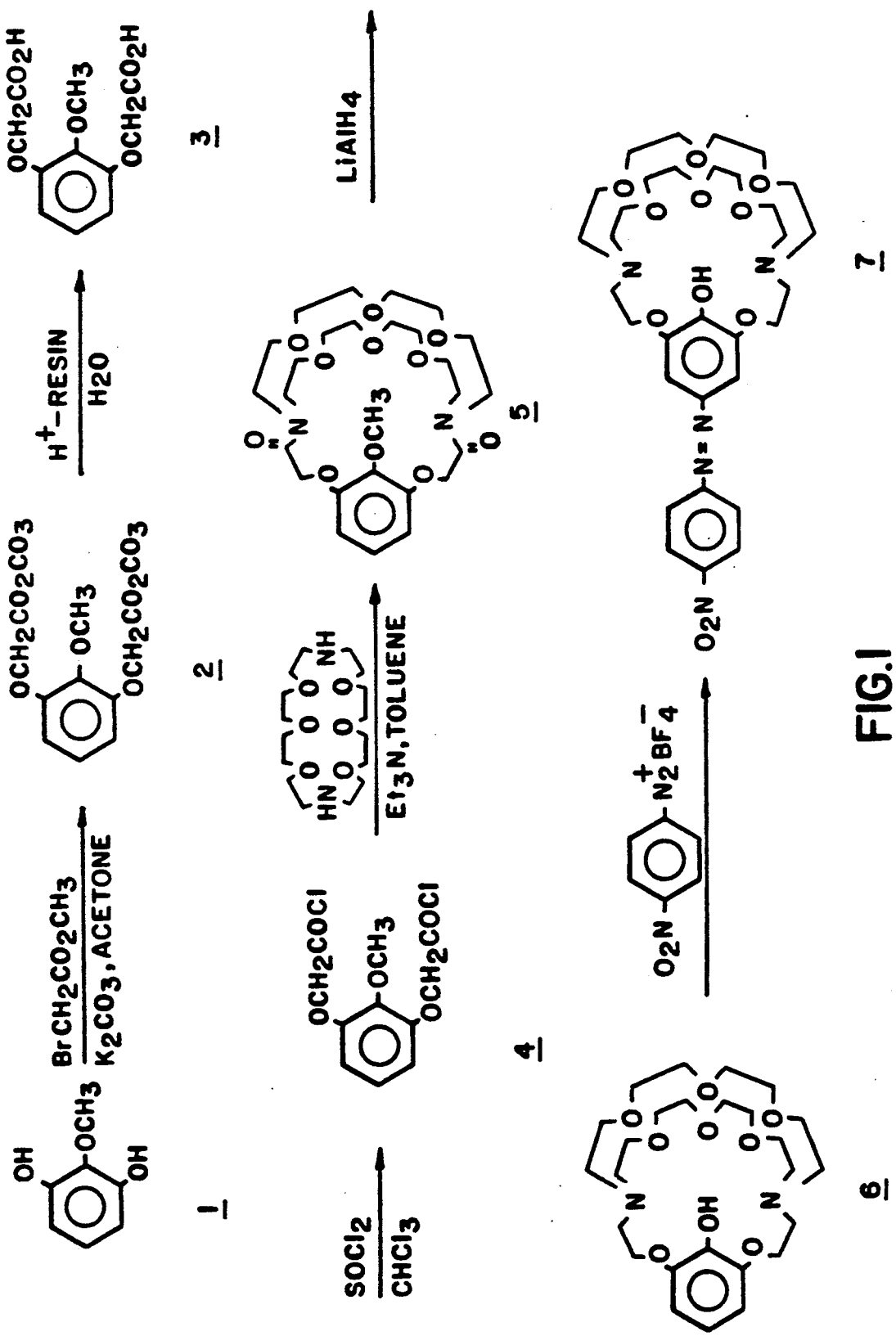
FIG. 1: Reaction pathway for synthesizing chromogenic cryptand 3.3.2.

The invention relates to compounds, reagents and methods for determining cations in a sample. The invention allows quantitative determination of cations in blood serum and other biological fluids by spectrophotometric technique in a homogeneous single phase solvent system that requires no sample pretreatment. The compounds are defined in formula I, and reagents preferably comprise compounds of formula I and may contain one or more interfering cation complexing compound masks. Suitable interfering cation complexing compound masks are non-chromogenic and include spherands, hemispherands, cryptahemispherands, cryptands and podands.

The compounds of this invention may be utilized in compositions for making cation determinations on automated clinical chemistry analyzers such as the Technicon CHEM-1 ® clinical chemistry analyzer, the Technicon RA-1000 ® clinical chemistry analyzer and the Technicon SMAC ® clinical chemistry analyzer. Additionally, the compounds of this invention may be utilized in compositions for making cation determinations on industrial or other non-clinical chemistry automated analyzers such as the Technicon TRAACS 800 TM analyzer. Moreover, the compounds of this invention may be utilized in compositions for making cation determinations by manual methods or standard UV/vis spectrophotometers.

In one embodiment of the invention, chromogenic cryptand 3.2.2 is particularly effective for potassium cation determination. In another embodiment of the invention, chromogenic cryptand 3.3.2 has good sodium cation selectivity. In another embodiment of the invention, reagents and methods of the invention are used for determining potassium ion concentration of a sample comprising a mixture of potassium and sodium ions. The sodium ion complexing compound mask prevents sodium ions from complexing with chromogenic cryptands, thereby providing favorable conditions for promoting chromogenic cryptand-potassium ion complex formation.

In another embodiment of the invention, compounds, reagents and methods of the invention are used for determining sodium ion concentration of a sample comprising a mixture of potassium and sodium ions. Determination of sodium ion concentration using compounds of the invention may be further improved using potassium ion complexing compound masks. The potassium ion complexing compound mask prevents potassium ions from complexing with chromogenic cryptands, thereby providing favorable conditions for promoting chromogenic cryptand-sodium ion complex formation.

The sample fluids on which cation determinations can be performed using the compounds and compositions of this invention include biological, physiological, industrial, environmental and other types of liquids. Of particular interest are biological fluids such as serum, plasma, urine, cerebrospinal fluids, saliva, milk, broth and other culture media and supernatants, as well as fractions of any of them. Other sources of sample fluid which are tested by conventional methods are also contemplated as within the meaning of the term "sample" as used herein, and can have ionic determinations performed on them in accordance with this invention.

The skilled artisan will recognize that the presence of other ionic species, i.e., calcium, magnesium, and lithium, may also be determined using the compounds and compositions of this invention. The chromogenic cryptands may be used to produce color in the visible range upon interaction with cations.

The solvent system consists of water and water miscible organic solvent in proportions to obtain maximum sensitivity but to avoid sample pretreatment, such as protein precipitation, extraction or phase separation.

Cyclic ethers, glycol ethers, amides, aliphatic alcohols with, for example, three to eight carbon atoms and/or sulfoxides possess excellent photometric properties and are suitable water-miscible organic solvents useful in the present invention.

Dioxane and tetrahydrofuran are particularly suitable as cyclic ethers, while ethylene glycol monoalkyl ethers, particularly methyl, ethyl, propyl and butyl cellosolve, are suitable as glycol ethers, and formamide, dimethylformamide (DMF), pyrrolidone and N-alkylpyrrolidones, e.g., N-methylpyrrolidone (NMP), are suitable as amides.

Aliphatic alcohols such as methanol and ethanol are also suitable, but better results are obtained in alcohols with three to eight carbon atoms such as isopropanol, n-propanol, butanols, amyl alcohols, hexanols, heptanols and octanols.

Dimethyl sulfoxide is also a suitable solvent. The water-dioxane solvent system has proved particularly advantageous.

It has been found that a large number of water-miscible organic solvents, such as, for example, acetone, methyl ethyl ketone and glacial acetic acid are unsuitable as reaction media.

The solvent system of the present invention differs from Klink, et al., which teaches suitable reagent solvent systems as including a water-miscible organic solvent in amounts achieving a water to organic solvent ratio of about 1:4 to 1:6.

The present invention teaches solvent systems of about 1:0.5 to 1:2, and preferably includes a surfactant and higher pH. The solvent system of the present invention obviates the need for removal of protein from a serum sample.

Other components may also be included in the compositions of this invention, such as buffers and stabilizers. Additional ion masks may be employed to remove the effect of interfering ionic species.

Because of the importance of maintaining pH at a specific level in making accurate cation determinations, buffer may be included in compositions of this invention for the purpose of controlling the pH. Suitable buffers for maintaining the pH include cyclohexylaminopropanesulfonic acid (CHAPS), cyclohexylaminoethanesulfonic acid (CHES), triethanolamine, diethanolamine, ethanolamine, 2-naphthalene sulfonic acid, and salicylic acid. Preferably, in making a cation determination, the pH of the composition is maintained at about 8-12.

The compositions of this invention may also include a surfactant in order to aid in protein solubilization. Surfactants are also used in many automated analyzers for hydraulic reasons. Suitable surfactants for use in the compositions of this invention include sorbitan monoleate (commercially available as Tween-80 ® from ICI Americas Co. of Wilmington, DE) and polyoxyethylene lauryl ether (commercially available as Brij-35 ® from ICI Americas Co. of Wilmington, DE).

Reagents of the invention are mixed with a sample to be tested. After mixing of reagent and sample, absorbance of the resulting solution is measured to determine concentration of the cation of interest.

The invention also includes reagents and methods for determining cations in a sample, wherein said method employs a reagent comprising a chromogenic cryptand, and a carrier matrix comprising a porous or wettable material. In a single layer format, the carrier matrix can be formed from materials such as paper, cardboard, porous polymers, polymer fiber and natural felts, and other suitable materials. Preferred as carrier matrix materials are filter paper, and porous high density polyethylene. In a multilayer analytical element format, the buffer can be stored in an upper layer and the cryptand in a lower layer in a superimposed laminar fashion. The matrices for these layers can be formed from materials such as gelatin, water soluble or water swellable polymers, and other suitable materials. In addition to those two layers, a spreading layer, a reflecting layer and a support material can be incorporated to form an integral analytical element.

The reagent may also comprise one or more interfering cation complexing compound masks.

In one embodiment of the invention, the sample is blood serum or plasma, the carrier matrix is a device that is a dimensionally stable, uniformly porous, diffusely reflective single layer formed of a polymeric non-fibrous matrix, and the method comprises the following steps:

(a) preparing a reagent mixture consisting essentially of one or more water-soluble polymeric binders, a surfactant, a compound according to formula I, water and a buffer;

(b) adding the reagent mixture to the device;

(c) evaporating the water of the reagent mixture;

(d) adding the sample to the device; and (e) measuring reflectance of the device.

In a preferred embodiment of the invention, the method comprises the following steps:

(a) preparing a reagent mixture comprising a first organic solvent having low vapor pressure and high boiling point, a second organic solvent that is more volatile than first solvent, a compound of formula I, and a buffer;

(b) adding the reagent mixture to the device;

(c) evaporating the second solvent of the reagent mixture;

(d) adding the sample to the device; and (e) measuring reflectance of the device.

The reagent may also comprise one or more interfering cation complexing compound masks.

Step (a) advantageously incorporates both solvents and the organic buffer in one step, and elminates the need for drying step between solvent addition and buffer addition.

Preferred reagents comprise a first solvent such as trialkylphosphate, triarylphosphate, dialkyladipate, dialkylsebacate, dialkylphthalate, and a second solvent such as cyclohexanone, tetrahydrofuran, dioxane, methanol and diethylether.

Preferred reagents comprise one or more water soluble polymeric binders selected from the group including polyvinyl alcohol, polyvinyl pyrrolidone, polyacrylic acid, methyl cellulose, hydroxymethylcellulose and gelatin.

Preferred reagents further comprise one or more organic buffers. Examples of suitable organic buffers include triethanolamine, diethanolamine, ethanolamine, 2-naphthalene sulfonic acid, salicylic acid, p-toluene sulfonic acid, CHAPS and CHES. Suitable buffers maintain a pH in the range of about 8 to about 12.

The matrix may be constructed in one of several ways. One suitable way involves sintering fine particulates of a high-density polyethylene, ultra-high molecular weight polyethylene, polypropylene, polyvinylidene fluoride, polytetrafluoroethylene, nylon, polyvinylchloride, polyesters, polysulfones and blends thereof. The matrix may be coated with a hydrophilic surfactant selected from the group including polyoxyethyleneoctyl phenols, polyoxyethylenenonyl phenols, and polyoxyethylenelauryl ethers. By incorporating a suitable carrier matrix with the reagent, cation determination can be done using such a device.

Such a device lends itself to dry storage when not in use, thus enabling long shelf-life, and can be pressed into service immediately simply by contacting it with a small portion of the test sample, be it blood, serum, urine or other aqueous solution to be assayed. It can take on such formats as a dip-and-read strip for urine or a test slide for use with an automatic blood analyzer, or can form a multilayer structure such as is described in U.S. Pat. Nos. 3,992,158 and 4,292,272.

It is desirable that the carrier matrix comprise a porous or wettable material. Thus, in a single layer format the carrier matrix can be formed from materials such as paper, cardboard, porous polymers, polymer fiber and natural felts, and other suitable materials. Especially preferred as carrier matrix materials are filter paper, and porous high density polyethylene. In a multilayer analytical element format, the buffer can be stored in an upper layer and the chromogenic cryptand in a lower layer in a superimposed laminar fashion. The matrices for these layers can be formed from materials such as gelatin, water soluble or water swellable polymers, and other suitable materials. In addition to these two layers, a spreading layer, a reflecting layer and a support material can be incorporated to form an integral analytical element.

The device is prepared by incorporating the carrier matrix with the test composition and, if desired, providing dried matrix with a support.

Thus the composition is applied to the matrix by inoculating the surface of the matrix or by dipping it into a solution of the composition. The thus-impregnated matrix can then be dried at room temperature or at elevated temperatures provided the temperature is not so high as to deleteriously affect the composition.

The dried, impregnated carrier matrix can then be mounted, if desired, on a suitable support such as a circumferential frame which leaves the matrix exposed to the middle; or the matrix can be mounted at one end of a plastic strip, the other end serving as a convenient handle.

In one embodiment of the invention, the test sample containing sodium is contacted with the surface of the test device and the detectable response is measured at 620 nm or other appropriate wavelength on a reflectometer. Experiments using varied known sodium concentrations yield a dose/response curve enabling clear correlation between changes in percent reflectance and sodium concentration in the millimolar range.

The following examples illustrate but are not intended to limit the scope of the present invention.

EXAMPLES

Example 1

A chromogenic cryptand 3.3.2 was synthesized by the reaction pathway of FIG. 1, and is shown as compound 7.

Bis(1,3-methylacetoxy)-2-methoxybenzene (2)

To a stirred mixture of anhydrous $K_2CO_3$ (30 g) and methyl bromoacetate (30.5 g, 0.20 mol) in 400 ml of acetone was added dropwise under nitrogen a solution of 2-methoxyresorcinol (1) in 100 ml of acetone. The mixture was refluxed for 30 h. Filtration of the inorganic material and evaporation of the solvent gave a residue which was column chromatographed on silica gel with methylene chloride-methanol (50:1) to afford 19.3 g (95%) of 2 as a colorless, viscous liquid which solidified during storage in the form of white crystals; M.P. 70°-72° C. Calcd. for $C_{13}H_{16}O_7$ (percent): C, 54.93; H, 5.67 Found: (percent): C, 54.82; H, 5.55.

1,3-Di(oxyacetic acid)-2-methoxybenzene (3)

Dimethylester 2 (4.00 g, 14 mmol) was suspended in 250 ml of water containing Amberlyst IR-120(H+) (0.5 g). The mixture was refluxed for 8 h. The resin was filtered and the water solution concentrated. A white crystalline material was separated and dried to give 3.33 g (93%) of diacid 3; M.P. 148°-150° C. (lit. mp 150°-152° C.).

Diacid Chloride 4

Diacid 3 (2.50 g. 9.8 mmol) was suspended in 15 ml of chloroform and the mixture was heated to reflux. Thionyl chloride (3 ml) was added dropwise to the refluxing suspension and it was refluxed overnight to give an almost clear solution. The reaction mixture was cooled, filtered, and evaporated in vacuo to afford 2.74 g (96%) of a pale yellow solid with mp 61.5°-63.5° C. which was used subsequently without purification.

Methoxybenzo Cryptand Diamide 5

To 225 ml of rapidly-stirred toluene at 0° C. under nitrogen were simultaneously added solutions of diacid chloride 4 (2.00 g, 6,8 mmol) in 90 ml of toluene and Kryptofix ® 3.3 (2.89 g, 6.8 mmol) and triethylamine (2.5 ml) in 88 ml of toluene during a 6 h period. After completion of the addition, the reaction mixture was stirred at room temperature overnight. The solid material was filtered and the filtrate was evaporated in vacuo. The residue was column chromatographed on alumina with ethyl acetate-methanol (20:1) as eluent to give 1.85 g (48%) of cryptand diamide 5 as a viscous colorless oil. Calcd. for $C_{27}H_{42}N_2O_{11}$ (percent): C,56.83; H,7.43. Found (percent): C,56.49; H,7.52.

Cryptand Phenol 6

The cryptand diamide 5 (1.05 g, 1.8 mmol) was added to a suspension of lithium aluminum hydride (0.57 g, 15.0 mmol) in tetrahydrofuran (60 ml) and the mixture was refluxed for 20 h. After cooling, 3.0 ml of 5% NaOH was added. The inorganic precipitate was filtered and washed several times with tetrahydrofuran and with chloroform followed by suspension in water and extraction with chloroform. The washings and extracts were combined and the solvent was removed in vacuo. The residue was dissolved in chloroform and the solution was washed with water several times and evaporated in vacuo to give 0.87 g (91%) of 6 as a viscous, extremely hygroscopic yellow oil. Calcd. for $C_{26}H_{44}N_2O_9 \cdot 0.75 H_2O$ (percent); c,57.60; H,8.46. Found (percent): C, 57.60; H,8.65.

Chromogenic Cryptand 7

To cryptand phenol 6 (1.18 g, 2.2 mmol) was added 32% NaOH until the aqueous solution was basic. The clear, brown-colored solution was evaporated to dryness in vacuo. Acetic acid (20 ml) was added to the residue to give a clear yellow solution which was cooled to 0° C. A solution of p-nitrobenzenediazonium tetrafluoroborate (0.59 g, 2.5 mmol) in water (30 ml) was added dropwise with vigorous stirring. After the addition was completed, the mixture was stirred overnight at room temperature and then evaporated to dryness. The residue was subjected to column chromatography on alumina with chloroform and then chloroform-ethanol (12:1) as eluents to give 1.10 g (73%) of 7 as a red-brown semi-solid. Calcd. for $C_{32}H_{47}N_5O_{11}$ 0.75 $H_2O$ (percent): C, 55.60; H, 7.07. Found (percent): C, 55.54; H, 7.00.

Notes:
1. Diacid 3 and diacid chloride 4 were described in Merck's patent: R. Klink, B. Bodar, J.-M. Lehn, B. Helfert, and R. Bitsch, West German Patent 3002779, Aug. 4, 1983.
2. Krypotfix ® 3.3. was prepared by literature procedure reported by B. Dietrich, J.-M. Lehn, J. P. Savage, and J. Blanzat, Tetrehedron, 29, 1629 (1973).

Among the advantages of this synthesis is that it avoids a messy and low yield reaction of pyrogallol with chlorcacetic acid. The first two steps are straightforward and almost quantitative. The synthesis pathway also accomplishes reduction of the bicyclic diamide and demethylation in one single step using $LiAlH_4$, and avoids the need for purification on a Dowex ($OH^-$) column. The pathway is shorter and gives higher yields than Merck's method.

EXAMPLE 2

Figure 2:
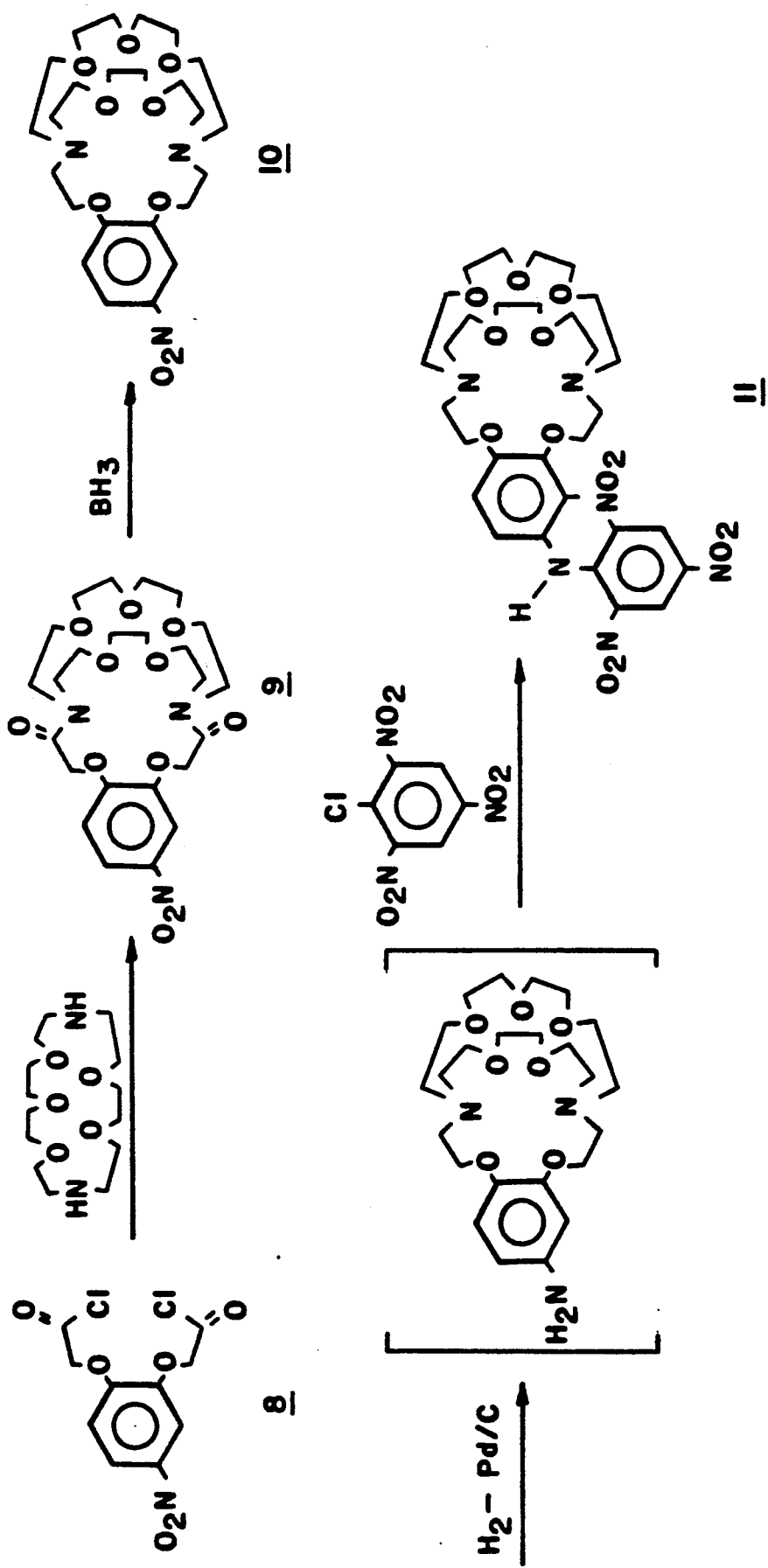
FIG. 2: Reaction pathway for synthesizing chromogenic benzocryptand 3.2.2.

A chromogenic benzocryptand 3.2.2 was synthesized by the reaction pathway of FIG. 2, and is shown as compound 11.

Cryptand Diamide 9

A 3000 ml 3-neck flask equipped with a mechanical stirrer and two syringe pumps was evacuated and filled with nitrogen. The flask was charged with toluene (265 ml) and cooled to 0° C. in an ice bath. Solution A consisting of Kryptofix ® 3.2 (2.10 g, 6.8 mmol) and triethylamine (1.80 g, 17.8 mmol) in 35 ml of toluene and Solution B consisting of diacid chloride 8 (prepared in accordance with Gansow, O. A.; Kausar, A. R.; Triplett, K. B. J. Heterocyclic Chem. 1981, 18,297) (2.11 g, 6.8 mmol) in 35 ml of toluene were added simultaneously to vigorously stirred toluene over 5 h. The mixture was stirred overnight at room temperature. The precipitated salt was filtered and the solvent was removed in vacuo to give a residue which was column chromotographed on an alumina column with chloroform-ethanol (100:2) to afford 1.00 g (27%) of 9 as a light yellow fluffy solid. Calcd. for $C_{24}N_{35}N_3O_{11}$ (percent): C,53.23; H, 6.51. Found (percent): C,53.00; H, 6.61.

Nitrocryptand 10

Cryptand diamide 9 (1.00 g, 1.85 mmol) was dissolved in 10 ml of dry tetrahydrofuran and 1.5 ml of 10M $BH_3$ $(CH_3)_2S$ complex was added. The mixture was refluxed overnight. Excess diborane was destroyed with water and the solvent was removed in vacuo. The residue was treated with 10 ml of 6N HCl at reflux for 7 h. Water was removed in vacuo and the dihydrochloride was passed through a Dowex ion exchange resin (OH form) to give 0.95 g (approximately 100%) of the crude product which was used in the next step without additional purification.

Chromogenic Cryptand 11

Nitrocryptand 10 (0.90 g, 1.75 mmol) was dissolved in 50 ml of ethyl acetate and palladium on carbon (10%) (0.3 g) was added. The mixture was shaken under 40 psi of hydrogen pressure at room temperature. The catalyst was filtered and the solvent was removed to give 0.82 g of a brown oil, which was dissolved in methanol (3 ml). To this solution sodium bicarbonate (0.3 g) and picryl chloride (0.5 g) were added. The mixture turned immediately red and was refluxed for 6 h. The solvent was removed in vacuo and the residue was column chromatographed on alumina with chloroform-ethanol (200:1) to produce 0.65 g (55%) of a dark red oil. Calcd. for $C_{30}H_{42}N_6O_{13}$ (percent) C, 51.87; H,6.0%. Found (percent): C,51.62, H,6.12.

EXAMPLE 3

An experiment was conducted to compare the present invention with a state-of-the-art method for measuring sodium in serum.

A series of random serum samples containing a broad range of sodium concentration was obtained. The samples were assayed in RA-1000 ® analyzer (Technicon Instruments Corporation) using the reagent formulation listed below:

| | |
|---|---|
| $1.35 \times 10^{-4}M$ | chromogenic cryptand 3.3.2 (compound 7 of FIG. 1) |
| $5 \times 10^{-3}M$ | EDTA (divalent ion mask) |
| pH 10 | CHES 0.15M (buffer) |
| 50% (v/v) | Ethoxyethoxyethanol (water miscible organic solvent) |
| 2% (w/v) | Tween ®-80 (surfactant) |

The parameters on the RA-1000 ® instrument were as follows.

| | |
|---|---|
| sensitivity | 3.2 mA/mM |
| method | end point |
| temperature | 37° C. |
| wavelength | 600 nm |
| sample volume | 8 µl |
| reagent volume | 385 µl |
| delay | 5 min. |
| pH | 10.0 |
| dilution ratio | 1:50 |

Result

The absorbance output from the RA-1000 ® instrument for each sample was recorded and converted to sodium concentrations. The same set of serum samples was also assayed by RA-1000 ISE ® module for sodium concentrations.

| Correlation data on RA-1000 ® Analyzer Reference method RA-1000 ISE ® | |
|---|---|
| slope | 1.00 |
| intercept | −3.17 |
| correlation coefficient | 0.9820 |
| number of serum samples | 53 |
| linear range, mM | 80–200 |
| precision, CV | 1.3% |

The data show good agreement between the method of the present invention and the state-of-the-art ISE ® methodology.

EXAMPLE 4

This example describes the use of chromogenic cryptand 3.3.2 for the assay of sodium in undiluted blood serum by dry chemistry technology. Dry reagent analytical elements were prepared in the following manner.

To each ½ inch diameter porous disk (HDPE, 35 μm, 1/32-inch thick), 30 microliters of a reagent mixture containing 1.0 ml cyclohexanone, 0.1 ml tricresyl phosphate, 10 mg cellulose acetate, 1 mg chromogenic cryptand 3.3.2 (compound 7 of FIG. 1), 30 mg triethanolamine, 9 mg 2-naphthalene sulfonic acid, and 5 mg Brij-35 were deposited, and the disks were allowed to dry at room temperature for five hours before storing in a desiccator for two hours.

The disks were tested with 25 microliters of a clinical specimen such as serum or plasma. The diffuse reflective signals after two minutes incubation were measured at 620 nm on a modified Infra-Alyzer (Technicon Instruments Corporation). The reflectance, R measurements were transformed to a linear function of sodium concentration

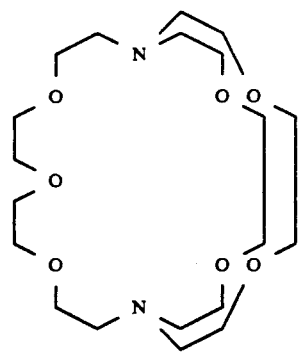

Chromogenic cryptand 3.2.2 is represented by

Figure 3:
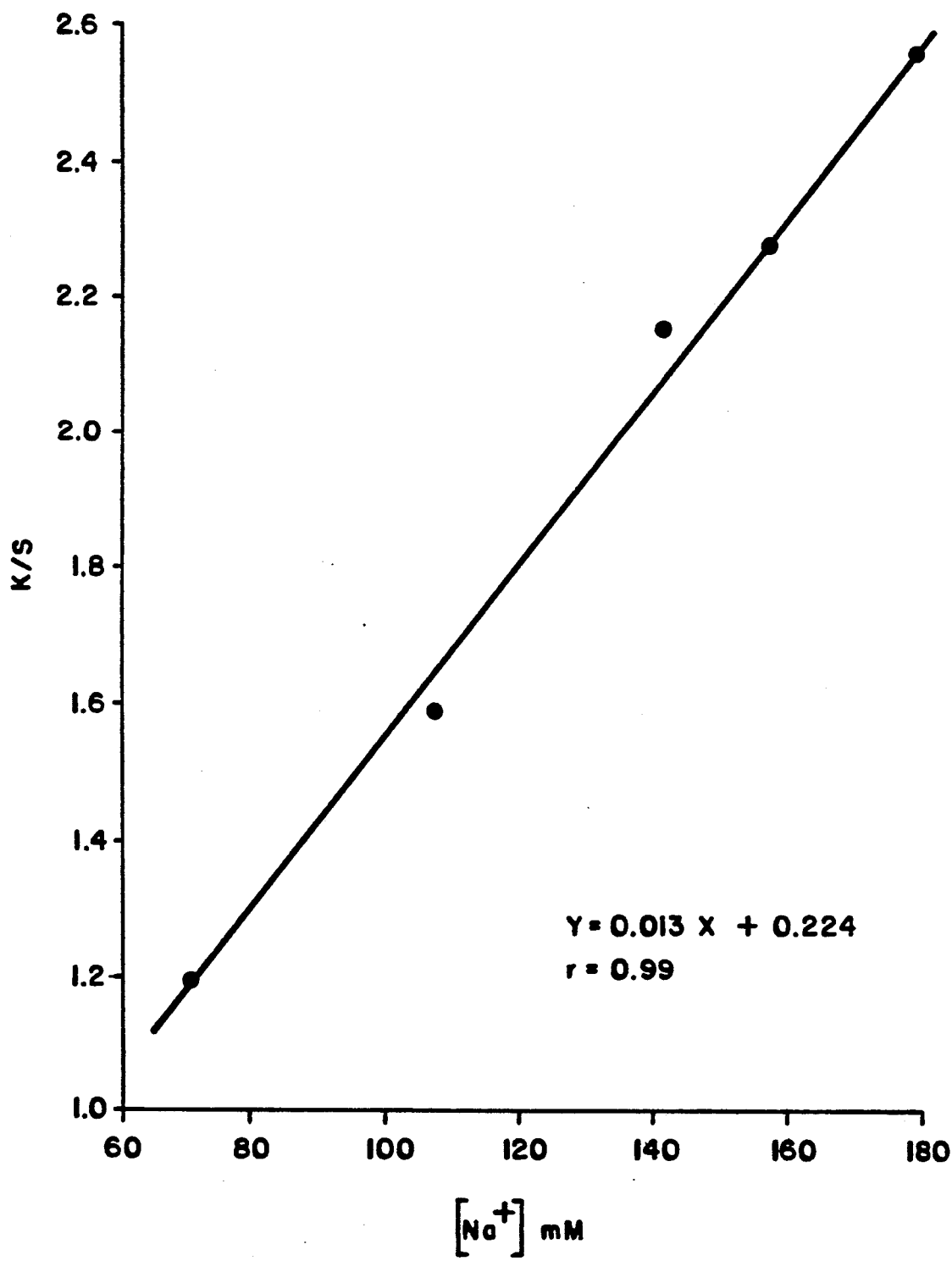
FIG. 3: Dry chemistry analytical element sodium response to chromogenic cryptand 3.3.2.

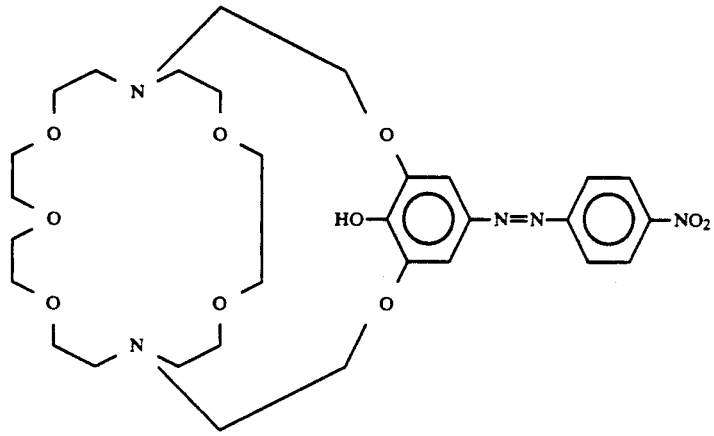

$$K/S = \frac{(1 - R)^2}{2R},$$

Where K is the absorption coefficient and S is the scattering coefficient. The plot of K/S versus sodium concentration is linear, as shown in FIG. 3.

EXAMPLE 5

An experiment was conducted to compare the present invention with a state-of-the-art method for measuring sodium in serum.

A series of random serum samples containing a broad range of sodium concentration was obtained. The samples were assayed on RA-1000 ® analyzer (Technicon Instruments Corporation) using the reagent formulation listed below:

| | |
|---|---|
| 1.35 × 10⁻⁴M | Chromogenic cryptand 3.2.2. |
| 2.0 × 10⁻³M | Cryptand 3.2.2. (potassium mask) |
| 5.0 × 10⁻³M | EDTA |
| 50% (v/v) | Ethoxyethoxyethanol |
| pH 11.2 | CAPS 0.15M |
| 2.5% (w/v) | Tween-80 ® |

Cryptand 3.2.2 is represented by

The parameters on the RA-1000 ® instrument were as follows:

| | |
|---|---|
| sensitivity | 1.7 mA/mM |
| method | end point |
| temperature | 37° C. |
| wavelength | 600 nm |
| sample volume | 4 μl |
| reagent volume | 395 μl |
| delay | 5 min. |
| pH | 11.2 |
| dilution ratio | 1:100 |

Result

The absorbance output from the RA-1000 ® instrument for each sample was recorded and converted to sodium concentrations. The same set of serum samples was also assayed by RA-1000 ISE ® module for sodium concentrations.

| Correlation data on RA-1000 ® analyzer Reference method RA-1000 ISE ® | |
|---|---|
| slope | 1.13 |
| intercept | −12.47 |
| correlation coefficient | 0.9505 |
| number of serum samples | 80 |
| Linear range mM | 80–200 |
| Precision, CV | 2.1% |

The data show good correlation between the method of the present invention and the state-of-the-art methodology.

EXAMPLE 6

An experiment was conducted to compare the present invention with a state-of-the-art method for measuring potassium in serum.

A series of random serum samples containing a broad range of potassium concentrations was obtained. The samples were assayed in RA-1000 ® analyzer (Technicon Instruments Corporation) using the reagent formulation listed below:

| | |
|---|---|
| $1.69 \times 10^{-4}$ M | chromogenic cryptand 3.2.2 |
| $3.0 \times 10^{-2}$ M | Kryptofix ® 2.1.1 |
| $4.0 \times 10^{-3}$ M | EDTA (divalent ion mask) |
| 60% (v/v) | Ethoxyethoxyethanol (water miscible organic solvent) |
| pH 11 | CAPS 0.12M (buffer) |
| 2.5% (w/v) | Tween-80 ® (surfactant) |

The parameters on the RA-1000 ® instrument were as follows:

| | |
|---|---|
| sensitivity | 12.0 mA/mM |
| method | end point |
| temperature | 37° C. |
| wavelength | 540 nm |
| sample volume | 4 µl |
| reagent volume | 395 µl |
| delay | 5 min. |
| pH | 11.5 |
| dilution ratio | 1:100 |

Result

The absorbance output from the RA-1000 ® analyzer for each sample was recorded and converted to potassium concentrations. The same set of serum samples was also assayed by RA-1000 ISE ® module for potassium concentrations.

| Correlation data on RA-1000 ® analyzer Reference method RA-1000 ISE ® | |
|---|---|
| slope | 1.10 |
| intercept | −0.26 |
| correlation coefficient | 0.9704 |
| number of serum samples | 41 |
| Linear range, mM | 0-14 |
| Precision, CV | 2.2% |

The data show good correlation between the method of the present invention and the state-of-the-art methodology.

EXAMPLE 7

An experiment was performed to determine the response of a chromogenic benzocryptand 3.2.2. (shown as compound 11 in FIG. 2) to potassium ions in aqueous test samples which also contained sodium ions in high concentration.

A 0.1 mM stock solution of chromogenic benzocryptand 3.2.2 was prepared by dissolving 6.9 mg in 100 ml methylene chloride solvent. A stock buffer solution was prepared by dissolving 2.52 g of HEPPS (N-hydroxyethyl-piperazine-N-3-propanesulfonic acid) in 90 ml deionized water, adjusting the pH to 8.0 with 1.0M, tetramethylammonium hydroxide and bringing the total volume to 100 ml with deionized water. A series of test samples was prepared by adding varying amounts of potassium chloride (potassium concentration range of 0-10 mM) and a constant amount of sodium chloride (sodium concentration of 140 mM) to the stock buffer solution.

To perform the assay, 2.0 ml of the stock chromogenic benzocryptand 3.2.2 and 1.0 ml of the test sample were pipetted in a test tube.

The mixture in the test tube was agitated for 1-2 min on a vortex mixer. The test tube was set aside to allow the two solvent phases to separate. Following the phase separation, the methylene chloride phase was transferred to an optical cuvette and the absorbance was measured at 450 nm wave length on a Beckman DU8 spectrophotometer.

The results of the experiment are reported as follows:

| TEST SAMPLES | | |
|---|---|---|
| POTASSIUM (mM) | SODIUM (mM) | ABSORBANCE AT 450 nm |
| 0 | 140 | 0.7667 |
| 2.0 | 140 | 1.0030 |
| 4.0 | 140 | 1.0965 |
| 6.0 | 140 | 1.1441 |
| 8.0 | 140 | 1.1980 |
| 10.0 | 140 | 1.2010 |

The results clearly indicate a response to potassium ions in the presence of very high concentration of sodium and hence the usefulness of chromogenic benzocryptand 3.2.2 in the quantitative determination of potassium in test samples such as blood serum without significant interference from high sodium concentrations.

What is claimed is:

1. A reagent for determining an amount of cations present in a sample, the reagent comprising:

a 3.2.2 or 3.3.2 chromogenic cryptand compound of the formula I

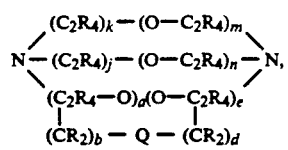

wherein k and j, either same or different, are equal to 1 to about 5;

m and n, either same or different, are equal to 0 to about 4;

a and e, either same or different, are equal to 0 to about 2;

b and d, either same or different, are equal to 0 to about 5;

R, either same or different, is hydrogen, lower alkyl, lower alkylidene, lower alkenyl, allyl, or aryl; and Q is

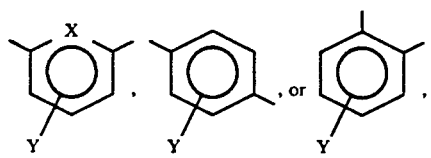

wherein
X is CH, N, or COH;
and Y includes

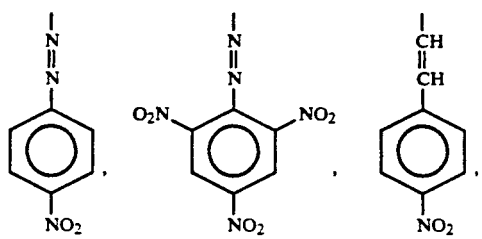

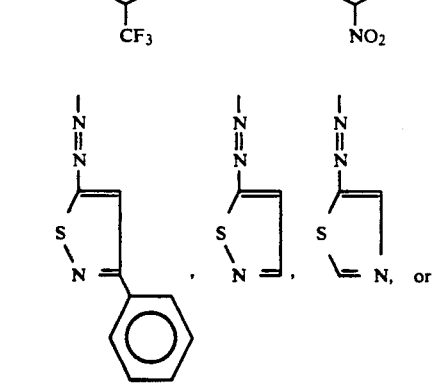

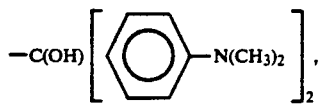

except that when Q is wherein Y is selected from the group consisting of p-nitrophenylazo, 3-phenyl-isothiazolyl-5-azo, isothiazolyl-5-azo, thiazolyl-5-azo, 2,4,6-trinitrophenylazo, p-nitro styryl, p-benzoquinonemonoimino and bis-(p-dimethylaminophenyl) hydroxymethyl, then the following conditions cannot be present: that simultaneously b is equal to 0 or 1, d is equal to 0 or 1, j is equal to 1, n is equal to 1 or 2, a is equal to 1, e is equal to 1, k is equal to 1, and m is equal to 2.

2. The reagent of claim 1, further comprising water and at least one buffer for maintaining the pH of the reagent at between about 8 and about 12.

3. The reagent of claim 2, wherein at least one buffer is an organic buffer selected from the group consisting of cyclohexylaminopropanesulfonic acid (CHAPS), cyclohexylaminoethanesulfonic acid (CHES), triethanolamine, diethanolamine, ethanolamine, 2-napthalene sulfonic acid, salicylic acid, and p-toluene sulfonic acid.

4. The reagent of claim 2, further comprising a water miscible organic solvent.

5. The reagent of claim 4, wherein the solvent is selected from the group consisting of cyclic ethers, glycol ethers, amides, aliphatic alcohols, sulfoxides, and mixtures thereof; and wherein the solvent has from three to eight carbon atoms.

6. The reagent of claim 4, further comprising a surfactant, and wherein the water to organic solvent ratio is between about 1:0.5 and about 1:2.

7. The reagent of claim 1, further comprising a first organic solvent having low vapor pressure and high boiling point, and a second organic solvent that is more volatile than the first solvent.

8. The reagent of claim 7, wherein the first organic solvent is selected from the group consisting of trialkylphosphate, triarylphosphate, dialkyladipate, dialkylsebacate, and dialkylphthalate, and wherein the second organic solvent is selected from the group consisting of cyclohexanone, tetrahydrofuran, dioxane, methanol, and diethylether.

9. The reagent of claim 7, further comprising a buffer suitable for maintaining reagent pH at between about 8 and about 12.

10. The reagent of claim 1, wherein the cryptand has selectivity for sodium cations in undiluted blood samples having a high concentration of sodium cations.

11. The reagent of claim 1, wherein the cryptand has selectivity for potassium cations in undiluted blood samples having a high concentration of sodium cations.

* * * * *